United States Patent
Metten et al.

(10) Patent No.: US 9,132,079 B2
(45) Date of Patent: *Sep. 15, 2015

(54) PRODUCT FOR KERATIN-CONTAINING FIBERS, CONTAINING AT LEAST A SPECIFIC COPOLYMER OF THE N-VINYLPYRROLIDONE AND AT LEAST A POLYMER WITH STRUCTURAL UNITS DERIVED FROM MALEIC ACID ESTER

(71) Applicant: Henkel AG & Co. KGaA, Dusseldorf (DE)

(72) Inventors: Diane Metten, Hamburg (DE); Bernd Richters, Hamburg (DE); Rene Scheffler, Ellerau (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,234

(22) PCT Filed: Nov. 20, 2012

(86) PCT No.: PCT/EP2012/073096
§ 371 (c)(1),
(2) Date: Jun. 17, 2014

(87) PCT Pub. No.: WO2013/092073
PCT Pub. Date: Jun. 27, 2013

(65) Prior Publication Data
US 2014/0369946 A1    Dec. 18, 2014

(30) Foreign Application Priority Data
Dec. 22, 2011 (DE) .......... 10 2011 089 628

(51) Int. Cl.
*A61Q 5/06* (2006.01)
*A61K 8/81* (2006.01)
*A61K 8/04* (2006.01)
*A61Q 5/12* (2006.01)

(52) U.S. Cl.
CPC .............. *A61K 8/8182* (2013.01); *A61K 8/046* (2013.01); *A61K 8/8164* (2013.01); *A61Q 5/06* (2013.01); *A61Q 5/12* (2013.01); *A61K 2800/594* (2013.01)

(58) Field of Classification Search
CPC ......... A61Q 5/06; A61Q 5/12; A61K 8/8164; A61K 8/046
USPC ............................................ 424/70.16, 70.15
See application file for complete search history.

(56) References Cited

U.S. PATENT DOCUMENTS 4,240,450 A * 12/1980 Grollier et al. ................ 132/209
2001/0022967 A1    9/2001 Brandt et al.

FOREIGN PATENT DOCUMENTS

| DE | 19738866 A1 | 3/1999 |
|---|---|---|
| DE | 19756454 C1 | 6/1999 |
| EP | 998908 A2 | 5/2000 |
| EP | 1800715 A1 | 6/2007 |
| WO | 9922698 A1 | 5/1999 |
| WO | 9922701 A1 | 5/1999 |
| WO | WO 2010/020500 | * 2/2010 |

OTHER PUBLICATIONS

English transation of the Patent No. WO 2010/020500 A2 dated Feb. 4, 2015.*
Database GNPD, "Styling Gel," Nov. 2011.
Database GNPD, "Leave-in Spray," Jul. 2007.
Database GNPD, "Styling Mouse," May 2006.
Database GNPD, "Re-Shaper Strong Hold Hairspray" Mar. 2011.
Database GNPD, "Catalyst" Jun. 2010.
International Search Report completed Nov. 25, 2013 in PCT/EP2012/073096.

* cited by examiner

*Primary Examiner* — Eisa Elhilo
(74) *Attorney, Agent, or Firm* — P. Scott Smith

(57) ABSTRACT

Agents for treating keratin-containing fibers, in particular human hair, and methods for the use of such agents are provided. The agent includes at least one copolymer (a) and at least one copolymer (b). The copolymer (a) includes at least one structural unit of a formula (I) and at least one structural unit of a formula (II). Copolymer (b) includes at least one structure unit of formula (AI) and at least one structural unit of formula (A2). The agent is contained in a cosmetically acceptable carrier.

17 Claims, No Drawings

PRODUCT FOR KERATIN-CONTAINING FIBERS, CONTAINING AT LEAST A SPECIFIC COPOLYMER OF THE N-VINYLPYRROLIDONE AND AT LEAST A POLYMER WITH STRUCTURAL UNITS DERIVED FROM MALEIC ACID ESTER

CROSS REFERENCE TO RELATED APPLICATIONS

The present disclosure is a U.S. National Stage entry under 35 U.S.C. §371 based on International Application No. PCT/EP2012/073096, filed Nov. 20, 2012, which was published under PCT Article 21(2) and which claims priority to German Patent Application No. DE 10 2011 089 628.7 filed on Dec. 22, 2011, which is incorporated herein by reference in its entirety.

TECHNICAL FIELD

The technical field relates to agents for treating hair containing a combination of at least one specific copolymer of N-vinylpyrrolidone with at least one polymer with structural units derived from maleic acid ester, to the use of these agents for temporarily deforming and/or for conditioning keratin-containing fibers and to aerosol hair sprays/mousses based on these agents.

BACKGROUND

Keratin-containing fibers are in principle taken to mean all kinds of animal hair, for example wool, horsehair, angora hair, furs, feathers and products or textiles manufactured therefrom. Preferably, however, the keratinic fibers are human hair.

An attractive hairstyle is today generally regarded as an indispensable part of a well-groomed appearance. Current fashion trends often mean that, with many hair types, hairstyles which are considered stylish can only be achieved or maintained for an extended period of up to several days by using setting active substances. Hair treatment agents which bring about permanent or temporary shaping of the hair accordingly play an important role. Temporary shaping, which is intended to provide a good hold without impairing the healthy appearance of the hair, such as for example the gloss thereof, may be achieved for example by hairsprays, hair waxes, hair gels, hair mousses, setting lotions etc.

Appropriate agents for temporary shaping conventionally contain synthetic polymers as the shaping component. Preparations which contain a dissolved or dispersed polymer may be applied to the hair by means of propellant gases or by a pump mechanism. Hair gels and hair waxes in particular are, however, not generally applied directly onto the hair, but are rather distributed in the hair by means of a comb or the hands.

The most important characteristic of an agent for temporarily deforming keratinic fibers, hereinafter also designated "styling agent", is to provide the strongest possible hold for treated fibers in the shape created. If the keratinic fibers are human hair, this is also referred to as strong styling hold or a high level of styling agent hold. Styling hold is substantially determined by the nature and quantity of the synthetic polymer used, but the further components of the styling agent may also have an influence.

In addition to a high degree of hold, styling agents must meet a whole series of further requirements. These may be broadly divided into properties on the hair, properties of the respective formulation, for example properties of the mousse, the gel or the sprayed aerosol, and properties which affect the handling of the styling agent, wherein properties on the hair are of particular importance. Particular mention should be made of moisture resistance, low tackiness and a well-balanced conditioning effect. Moreover, a styling agent should as far as possible be universally applicable to all hair types.

To meet the various requirements, a plurality of synthetic polymers have already been developed which are used in styling agents. The polymers can be subdivided into cationic, anionic, nonionic and amphoteric film-forming and/or setting polymers. When applied to the hair, the polymers ideally result in a polymer film, which on the one hand imparts a strong hold to the hairstyle, but on the other hand is sufficiently flexible not to break when stressed. If the polymer film is too brittle, "film flakes" form, i.e. residues which detach on movement of the hair and create the impression that the user of the corresponding styling agent has dandruff.

Developing styling agents which combine all the desired properties has always been and remains problematic. This is true in particular of the combination of strong hold on the one hand and simple, uniform application to the keratin-containing fibers on the other hand.

Accordingly, it is desirable to provide an agent for temporarily deforming and/or conditioning keratinic fibers, which agent is distinguished by a high level of hold or by an elevated conditioning effect and in particular excellent handling characteristics during application to the keratin-containing fibers.

It has surprisingly been found that this can be achieved by a combination of specific polymers. In addition to these excellent properties it has moreover proved possible, in the context of specific embodiments, to provide compositions which do not exhibit turbidity. Freedom from turbidity is particularly relevant in the context of providing aerosol compositions, since solid suspended particles may lead to clogging of the discharge nozzle of the aerosol packaging. In general, turbid, low-viscosity compositions exhibit the additional risk of sedimentation, which has a disadvantageous effect on the storage stability of the composition.

SUMMARY

Agents for cosmetic treatment of keratin-containing fibers, in particular human hair, and methods for the use of such agents are provided. An agent for cosmetic treatment of hair includes at least one copolymer (a) and at least one copolymer (b). The copolymer (a) includes at least one structural unit of a formula (I) and at least one structural unit of a formula (II). Copolymer (b) includes at least one structure unit of formula (AI) and at least one structural unit of formula (A2). The agent is contained in a cosmetically acceptable carrier.

A method for temporarily deforming hair and/or for hair care is provided in another embodiment. The method includes Applying an agent to the hair, where the agent includes at least one copolymer (a) and at least one copolymer (b). The copolymer (a) includes at least one structural unit of a formula (I) and at least one structural unit of a formula (II). Copolymer (b) includes at least one structure unit of formula (AI) and at least one structural unit of formula (A2).

DETAILED DESCRIPTION

In an exemplary embodiment, a cosmetic agent for cosmetic treatment of keratin-containing fibers, in particular human hair, contains in a cosmetically acceptable carrier (a) at least one copolymer comprising at least one structural unit of formula (I) and at least one structural unit of formula (II),

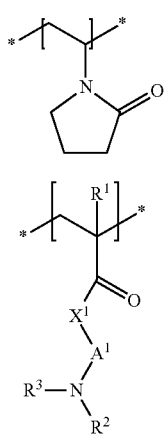

(I)

(II)

in which
R¹ denotes a hydrogen atom or a methyl group,
X¹ denotes an oxygen atom or an NH group,
A¹ denotes an ethane-1,2-diyl, propane-1,3-diyl or butane-1,4-diyl group,
R² and R³ mutually independently denote a ($C_1$ to $C_4$) alkyl group,
and
(b) at least one copolymer comprising at least one structural unit of formula (A1) and at least one structural unit of formula (A2)

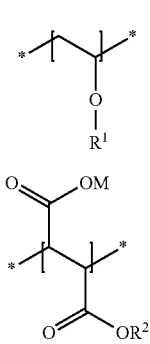

(A1)

(A2)

in which
R¹ denotes a ($C_1$ to $C_{18}$) alkyl group,
R² denotes a ($C_1$ to $C_6$) alkyl group,
M denotes a hydrogen atom or an equivalent of a mono- or polyvalent cation.

According to the above formulae and all the following formulae, a chemical bond characterized by the symbol * denotes a free valence of the corresponding structural fragment.

The positive polymer charge in the agent may be offset using any possible physiologically acceptable anions, such as for example chloride, bromide, hydrogensulfate, methylsulfate, ethylsulfate, tetrafluoroborate, phosphate, hydrogenphosphate, dihydrogenphosphate or p-toluenesulfonate, triflate.

Examples of ($C_1$-$C_4$) alkyl groups are methyl, ethyl, propyl, isopropyl, butyl, sec-butyl, isobutyl, tert-butyl.

Examples of ($C_8$ to $C_{30}$) alkyl groups are octyl (capryl), decyl (caprinyl), dodecyl (lauryl), tetradecyl (myristyl), hexadecyl (cetyl), octadecyl (stearyl), eicosyl (arachyl), docosyl (behenyl).

Examples of ($C_4$ to $C_{12}$) alkylaminocarbonyl groups are butylaminocarbonyl, sec-butylaminocarbonyl, isobutylaminocarbonyl, tert-butylaminocarbonyl, (2,4,4-trimethylpent-2-yl)aminocarbonyl, neopentylaminocarbonyl, 2-ethylhexylaminocarbonyl, neodecylaminocarbonyl.

Examples of ($C_4$ to $C_{12}$) alkylaminoethylaminocarbonyl groups are butylaminoethylaminocarbonyl, sec-butylaminoethylaminocarbonyl, isobutylamino-ethylaminocarbonyl, tert-butylaminoethylaminocarbonyl, (2,4,4-trimethylpent-2-yl)aminoethylaminocarbonyl, neopentylaminoethylaminocarbonyl, 2-ethyl-hexylaminoethylaminocarbonyl, neodecylaminoethylaminocarbonyl.

Examples of ($C_4$ to $C_{12}$) alkylaminopropylaminocarbonyl groups are butylaminopropylaminocarbonyl, sec-butylaminopropylaminocarbonyl, isobutyl-aminopropylaminocarbonyl, tert-butylaminopropylaminocarbonyl, (2,4,4-trimethylpent-2-yl)aminopropylaminocarbonyl, neopentylaminopropylaminocarbonyl, 2-ethylhexylaminopropylaminocarbonyl, neodecylaminopropylaminocarbonyl.

Examples of ($C_4$ to $C_{12}$) alkoxycarbonyl groups are butyloxycarbonyl, sec-butyloxycarbonyl, isobutyloxycarbonyl, tert-butyloxycarbonyl, (2,4,4-trimethylpent-2-yl)oxycarbonyl, neopentyloxycarbonyl, 2-ethylhexyloxycarbonyl, neodecyloxycarbonyl.

Examples of ($C_4$ to $C_{12}$) alkylaminoethyloxycarbonyl groups are butylaminoethyloxycarbonyl, sec-butylaminoethyloxycarbonyl, isobutylamino-ethyloxycarbonyl, tert-butylaminoethyloxycarbonyl, (2,4,4-trimethylpent-2-yl)aminoethyloxycarbonyl, neopentylaminoethyloxycarbonyl, 2-ethylhexyl-aminoethyloxycarbonyl, neodecylaminoethyloxycarbonyl.

Examples of ($C_4$ to $C_{12}$) alkylaminopropyloxycarbonyl groups are butylaminopropyloxycarbonyl, sec-butylaminopropyloxycarbonyl, isobutylamino-propyloxycarbonyl, tert-butylaminopropyloxycarbonyl, (2,4,4-trimethylpent-2-yl)aminopropyloxycarbonyl, neopentylaminopropyloxycarbonyl, 2-ethyl-hexylaminopropyloxycarbonyl, neodecylaminopropyloxycarbonyl.

Examples of ($C_4$-$C_{12}$) alkyl groups are butyl, sec-butyl, isobutyl, tert-butyl, 2,4,4-trimethylpent-2-yl, neopentyl, 2-ethylhexyl, neodecyl.

Examples of ($C_2$ to $C_{12}$) acyloxy groups are acetoxy, propionyloxy and neodecanoyloxy.

Preferred agents contain the copolymers (a) in a quantity of about 0.05 wt. % to about 8.0 wt. %, more preferably of about 0.1 wt. % to about 5.0 wt. %, particularly preferably of about 0.2 to about 2.5 wt. %, in each case relative to the total weight of the agent.

Preferred agents contain the copolymers (b) in a quantity of about 0.05 wt. % to about 8.0 wt. %, more preferably of about 0.1 wt. % to about 5.0 wt. %, particularly preferably of about 0.2 to about 2.5 wt. %, in each case relative to the total weight of the agent.

A preferably suitable cosmetic agent contains the amphiphilic, cationic polymers of component (a) and the component (b) copolymers in a weight ratio range of (a):(b) of about 5:1 to about 1:5, in particular of about 2:1 to about 1:2.

The properties of the agents prove particularly advantageous when it is formulated as an aerosol spray, aerosol mousse, pump spray or pump mousse. This preferred form of formulation is described in detail below.

The component (a) copolymers preferably have an average molecular weight $M_w$ (weight-average) of about 50000 g/mol to about 50000000 g/mol, in particular of about 250000 g/mol to about 3000000 g/mol, more preferably of about 750000 g/mol to about 2000000 g/mol.

Said weight-average is an average molecular weight which takes account of the total weight of the molecules of different molecular weight and not merely of the number of molecules. The "weight fraction"

$$w_i = (N_i M_i)/[\Sigma(N_i M_i)]$$

is first defined in order to calculate the weight average statistically. This indicates the proportion by weight of macromolecules in the sample which consist of i segments (e.g. monomer building blocks) of mass $M_i$ and occur $N_i$ times in the sample. The following equation accordingly applies to the weight-average molecular weight $M_w = \Sigma w_i M_i$ $M_w = [\Sigma(N_i M_i^2)]/[\Sigma(N_i M_i)]$.

The following component (a) copolymers are preferably used in the agents according to exemplary embodiments when the copolymers (a) fulfill one or more of the following features with regard to the above-stated formulae (I) and (II):

$R^1$ means a methyl group, $X^1$ denotes an oxygen atom, $A^1$ denotes ethane-1,2-diyl or propane-1,3-diyl, in particular ethane-1,2-diyl, $R^2$ and $R^3$ mutually independently denote methyl or ethyl (more preferably methyl).

It is preferred to select the structural unit of formula (II) from at least one structural unit of formula (II-1) to (II-4)

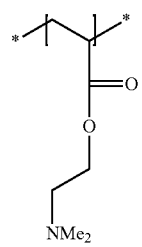

(II-1)

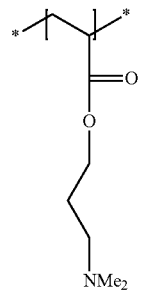

(II-2)

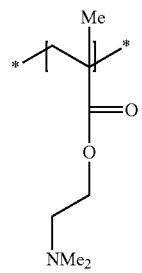

(II-3)

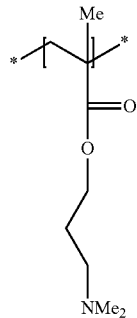

(II-4)

It has moreover proven more preferable to select the structural unit according to formula (II-3) and/or of formula (II-4) as the structural unit of formula (II). The structural unit of formula (II-3) is a particularly preferred structural unit.

A particularly preferred component (a) copolymer is the copolymer of N-vinylpyrrolidone and N,N-dimethylaminoethyl methacrylate (INCI name: VP/Dimethylaminoethyl Methacrylate Copolymer), which is distributed for example under the trade name Copolymer 937 (20 wt. % active substance in ethanol/water mixture, average molecular weight ($M_w$) 1000000) by ISP or Ashland.

In addition to said component (a) copolymer, the agent necessarily contains as component (b) at least one previously defined polymer with structural units derived from maleic acid ester (see above). This said polymer does of course differ from the component (a) compounds.

It is preferable for $R^1$ according to formula (A1) to denote a methyl group.

It is preferred for $R^2$ according to formula (A2) to denote a ($C_2$ to $C_4$) alkyl group, in particular ethyl, n-propyl, isopropyl, n-butyl or tert-butyl.

If the structural units of formula (A2) are present with a carboxylic acid function, the residue M denotes a hydrogen atom. If the structural units of formula (A2) assume salt form, M denotes an equivalent of a mono- or polyvalent cation. The mono- or polyvalent cation $M^{z+}$ with in each case a charge number z of one or higher merely serves for reasons of electroneutrality to compensate for the single negative charge of the carboxylate fragment —COO$^-$ of formula (A2) present in the case of salt formation. The equivalent of the corresponding cation to be used for this purpose amounts to 1/z. The fragment —COOM of formula (A2) denotes in the case of salt formation the group:

—COO$^-$ 1/z($M^{z+}$).

Mono- or polyvalent cations $M^{z+}$ which may in principle be considered are any physiologically acceptable cations. In particular, these are metal cations of the physiologically acceptable metals from groups Ia, Ib, IIa, IIb, IIIb, VIa or VIII of the periodic table of elements, ammonium ions, and cationic organic compounds with a quaternized nitrogen atom. The latter are formed for example by protonation of primary, secondary or tertiary organic amines (in particular ($C_2$ to $C_6$) alkanolamines (see below: neutralization of said polymers with ($C_2$ to $C_6$) alkanolamines)) with an acid, such as for example with structural units of formula (A2) in their acidic form, or by permanent quaternization of said organic amines. Examples of these cationic organic ammonium compounds are 2-ammonioethanol and 2-trimethylammonioethanol. In formula (A2), M preferably denotes a hydrogen atom, an ammonium ion, an alkali metal ion or a hydroxy-($C_2$ to $C_6$)-alkylammonium ion, more preferably a hydrogen atom, an ammonium ion, a hydroxy-$(C_2$ to $C_6)$-alkylammonium ion, a sodium ion or a potassium ion.

It is preferred for the agents to contain as component (b) at least one polymer of the group comprising polymers of the INCI nomenclature Butyl Ester of PVM/MA Copolymer, Isopropyl Ester of PVM/MA Copolymer, Ethyl Ester of PVM/MA Copolymer.

Corresponding component (b) polymers of the agent are distributed for example under the trade name Gantrez® ES 425 (copolymer of methyl vinyl ether and the butyl semi-ester of maleic acid; 50 wt. % active substance in ethanol; INCI name: Butyl Ester of PVM/MA Copolymer (Ashland)), Gantrez® ES 435 (copolymer of methyl vinyl ether and the butyl semi-ester of maleic acid; 50 wt. % active substance in isopropanol; INCI name: Butyl Ester of PVM/MA Copolymer (Ashland)), Gantrez® ES 3351 (copolymer of methyl vinyl ether and the isopropyl semi-ester of maleic acid; 50 wt. % active substance in isopropanol; INCI name: Butyl Ester of PVM/MA Copolymer (Ashland)), Gantrez® ES 225 (copolymer of methyl vinyl ether and the ethyl semi-ester of maleic acid; 50 wt. % active substance in ethanol); INCI name: Ethyl Ester of PVM/MA Copolymer (Ashland)).

The following embodiments of the cosmetic agents are particularly suitable for achieving the object:

(A) An agent for cosmetic treatment of keratin-containing fibers, in particular human hair, containing in a cosmetically acceptable carrier (a) at least one copolymer comprising at least one structural unit of formula (I) and at least one structural unit of formula (II),

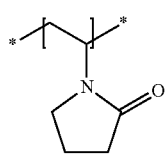

(I)

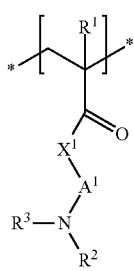

(II)

$R^1$ means a methyl group, $X^1$ denotes an oxygen atom, $A^1$ denotes ethane-1,2-diyl or propane-1,3-diyl, in particular ethane-1,2-diyl, $R^2$ and $R^3$ mutually independently denote methyl or ethyl (more preferably methyl), and (b) at least one copolymer comprising at least one structural unit of formula (A1) and at least one structural unit of formula (A2)

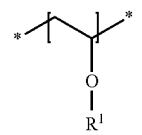

(A1)

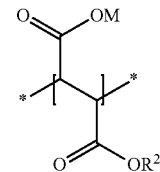

(A2)

in which $R^1$ denotes a methyl group, $R^2$ denotes an ethyl group, an n-propyl group, an isopropyl group, an n-butyl group or a tert-butyl group, M denotes a hydrogen atom or an equivalent of a mono- or polyvalent cation.

(B) An agent for cosmetic treatment of keratin-containing fibers, in particular human hair, containing in a cosmetically acceptable carrier (a) at least one copolymer with the INCI nomenclature VP/Dimethylaminoethyl Acrylate Copolymer and (b) at least one copolymer selected from at least one polymer of the group with polymers of the INCI nomenclature Butyl Ester of PVM/MA Copolymer, Isopropyl Ester of PVM/MA Copolymer, Ethyl Ester of PVM/MA Copolymer.

(C) An agent for cosmetic treatment of keratin-containing fibers, in particular human hair, containing in a cosmetically acceptable carrier (a) about 0.05 wt. % to about 8.0 wt. %, preferably from about 0.1 wt. % to about 5.0 wt. %, more preferably from about 0.2 to about 2.5 wt. %, of at least one copolymer comprising at least one structural unit of formula (I) and at least one structural unit of formula (II), (I)

(II)

$R^1$ means a methyl group, $X^1$ denotes an oxygen atom, $A^1$ denotes ethane-1,2-diyl or propane-1,3-diyl, in particular ethane-1,2-diyl, $R^2$ and $R^3$ mutually independently denote methyl or ethyl (more preferably methyl), and
(b) about 0.05 wt. % to about 8.0 wt. %, preferably from about 0.1 wt. % to about 5.0 wt. %, more preferably from about 0.2 to about 2.5 wt. %, of at least one copolymer comprising at least one structural unit of formula (A1) and at least one structural unit of formula (A2)

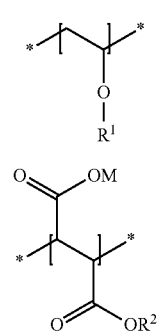

in which
R$^1$ denotes a methyl group,
R$^2$ denotes an ethyl group, an n-propyl group, an isopropyl group, an n-butyl group or a tert-butyl group,
M denotes a hydrogen atom or an equivalent of a mono- or polyvalent cation.
(D) An agent for cosmetic treatment of keratin-containing fibers, in particular human hair, containing in a cosmetically acceptable carrier
(a) about 0.05 wt. % to about 8.0 wt. %, preferably from about 0.1 wt. % to about 5.0 wt. %, more preferably from about 0.2 to about 2.5 wt. %, of at least one copolymer with the INCI nomenclature VP/Dimethylaminoethyl Acrylate Copolymer
and
(b) about 0.05 wt. % to about 8.0 wt. %, preferably from about 0.1 wt. % to about 5.0 wt. %, more preferably from about 0.2 to about 2.5 wt. %, of at least one copolymer selected from at least one polymer of the group with polymers of the INCI nomenclature Butyl Ester of PVM/MA Copolymer, Isopropyl Ester of PVM/MA Copolymer, Ethyl Ester of PVM/MA Copolymer.

In the context of the above embodiments (A) to (D), it is in turn more preferable for the component (a) copolymers to have an average molecular weight $M_w$ (weight-average) of about 50000 g/mol to about 50000000 g/mol, preferably of about 250000 g/mol to about 3000000 g/mol, more preferably of about 750000 g/mol to about 2000000 g/mol.

It is more preferable if, for all the embodiments of this first subject matter, the component (b) copolymers are present entirely or partially neutralized in salt form. At least one ($C_2$ to $C_6$) alkanolamine is preferably used for neutralization. For this reason, preferred agents (in particular the preferred embodiments (A) to (D)) additionally contain at least one ($C_2$ to $C_6$) alkanolamine. The alkanolamines usable as an alkalizing agent are preferably selected from primary amines with a $C_2$-$C_6$ alkyl parent substance which bears at least one hydroxyl group. Particularly preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Particularly preferred alkanolamines are selected from the group 2-aminoethan-1-ol, 2-amino-2-methylpropan-1-ol and 2-amino-2-methylpropan-1,3-diol.

The agents preferably have at 20° C. a pH value of about pH 4 to about pH 9, more preferably of about pH 6 to about pH 7.

To intensify the effect, the agents preferably additionally contain at least one surfactant, wherein in principle nonionic, anionic, cationic and ampholytic surfactants are suitable. The group of ampholytic or also amphoteric surfactants comprises zwitterionic surfactants and ampholytes. The surfactants may already have an emulsifying action. The additional surfactants are present in the agent according preferably in a quantity of about 0.01 wt. % to about 5 wt. %, more preferably of about 0.05 wt. % to about 0.5 wt. %, in each case relative to the weight of the agent.

It has proven more preferable for the agents additionally to contain at least one nonionic surfactant.

Nonionic surfactants contain as hydrophilic group for example a polyol group, a polyalkylene glycol ether group or a combination of a polyol group and polyglycol ether group. Such compounds are for example
  addition products of about 2 to about 100 mol of ethylene oxide and/or about 1 to about 5 mol of propylene oxide onto linear and branched fatty alcohols with about 8 to about 30 carbon (C) atoms, onto fatty acids with about 8 to about 30 C atoms and onto alkylphenols with about 8 to about 15 C atoms in the alkyl group,
  addition products, end group-terminated with a methyl or $C_2$-$C_6$ alkyl residue, of about 2 to about 50 mol of ethylene oxide and/or about 1 to about 5 mol of propylene oxide onto linear and branched fatty alcohols having about 8 to about 30 carbon atoms, onto fatty acids having about 8 to about 30 C atoms and onto alkylphenols having about 8 to about 15 C atoms in the alkyl group, such as for example the grades obtainable under the commercial names Dehydol® LS, Dehydol® LT (Cognis),
  $C_{12}$-$C_{30}$ fatty acid mono- and diesters of addition products of about 1 to about 30 mol of ethylene oxide onto glycerol,
  addition products of about 5 to about 60 mol of ethylene oxide onto castor oil and hardened castor oil,
  polyol fatty acid esters, such as for example the commercial product Hydagen® HSP (Cognis) or Sovermol grades (Cognis),
  alkoxylated triglycerides,
  alkoxylated fatty acid alkyl esters of formula (E4-I)

in which R$^1$CO denotes a linear or branched, saturated and/or unsaturated acyl residue having about 6 to about 22 carbon atoms, R$^2$ denotes hydrogen or methyl, R$^3$ denotes linear or branched alkyl residues having 1 to about 4 carbon atoms and w denotes numbers from 1 to about 20,
  amine oxides,
  hydroxy mixed ethers, as are for example described in DE-OS 19738866,
  sorbitan fatty acid esters and addition products of ethylene oxide onto sorbitan fatty acid esters such as for example polysorbates,
  sugar fatty acid esters and addition products of ethylene oxide onto sugar fatty acid esters,
  addition products of ethylene oxide onto fatty acid alkanolamides and fatty amines, sugar surfactants of the alkyl and alkenyl oligoglycoside type according to formula (E4-II), $$R^4O\text{-}[G]_p \tag{E4-II}$$

in which $R^4$ denotes an alkyl or alkenyl residue having about 4 to about 22 carbon atoms, G denotes a sugar residue having about 5 or about 6 carbon atoms and p denotes numbers from 1 to 10. They may be obtained in accordance with the relevant methods of preparative organic chemistry.

Particularly preferred nonionic surfactants have proved to be alkylene oxide addition products onto saturated linear fatty alcohols and fatty acids with in each case about 2 to about 100 mol of ethylene oxide per mol of fatty alcohol or fatty acid respectively. Preparations with excellent properties are likewise obtained if they contain as nonionic surfactants $C_{12}$-$C_{30}$ fatty acid mono- and diesters of addition products of about 1 to about 30 mol of ethylene oxide onto glycerol and/or addition products of about 5 to about 60 mol of ethylene oxide onto castor oil and hardened castor oil.

Particularly preferably, the agents contain as surfactant at least one addition product of about 15 to about 100 mol of ethylene oxide, in particular of about 15 to about 50 mol of ethylene oxide onto a linear or branched (in particular linear) fatty alcohol with 8 to 22 carbon atoms. This is particularly preferably Ceteareth-15, Ceteareth-25 or Ceteareth-50, which are marketed as Eumulgin® CS 15 (COGNIS), Cremophor A25 (BASF SE) or Eumulgin® CS 50 (COGNIS).

Anionic surfactants which are suitable in principle are any anionic surface-active substances suitable for use on the human body. These are characterized by an anionic water-solubilizing group such as for example a carboxylate, sulfate, sulfonate or phosphate group and a lipophilic alkyl group having about 8 to about 30 C atoms. The molecule may additionally contain glycol or polyglycol ether groups, ester, ether and amide groups and hydroxyl groups. Examples of suitable anionic surfactants are, in each case in the form of sodium, potassium and ammonium and the mono-, di- and trialkanolammonium salts having about 2 to about 4 C atoms in the alkanol group, linear and branched fatty acids with about 8 to about 30 C atoms (soaps),
ether carboxylic acids of formula R—O—(CH$_2$—CH$_2$O)$_x$—CH$_2$—COOH, in which R is a linear alkyl group having about 8 to about 30 C atoms and x=0 or 1 to 16,
acyl sarcosides having about 8 to about 24 C atoms in the acyl group,
acyl taurides having about 8 to about 24 C atoms in the acyl group,
acyl isethionates having about 8 to about 24 C atoms in the acyl group,
sulfosuccinic acid mono- and dialkyl esters having about 8 to about 24 C atoms in the alkyl group and sulfosuccinic acid monoalkyl polyoxyethyl esters having about 8 to about 24 C atoms in the alkyl group and 1 to about 6 oxyethyl groups,
linear alkane sulfonates having about 8 to about 24 C atoms,
linear alpha-olefin sulfonates having about 8 to about 24 C atoms,
alpha-sulfofatty acid methyl esters of fatty acids having about 8 to about 30 C atoms,
alkyl sulfates and alkyl polyglycol ether sulfates of formula R—O(CH$_2$—CH$_2$O)$_x$—OSO$_3$H, in which R is a preferably linear alkyl group having about 8 to about 30 C atoms and x=0 or 1 to 12,
mixtures of surface-active hydroxysulfonates,
sulfated hydroxyalkyl polyethylene glycol ethers and/or hydroxyalkylene propylene glycol ethers,
sulfonates of unsaturated fatty acids having about 8 to about 24 C atoms and 1 to about 6 double bonds,
esters of tartaric acid and citric acid with alcohols, which are addition products of about 2-15 molecules of ethylene oxide and/or propylene oxide onto fatty alcohols having about 8 to about 22 C atoms,
sulfated fatty acid alkylene glycol esters of formula (E1-II)

$$R^7CO(AlkO)_nSO_3M \tag{E1-II}$$

in which $R^7CO$— denotes a linear or branched, aliphatic, saturated and/or unsaturated acyl residue with about 6 to about 22 C atoms, Alk denotes CH$_2$CH$_2$, CHCH$_3$CH$_2$ and/or CH$_2$CHCH$_3$, n denotes numbers from about 0.5 to about 5 and M denotes a cation, as they are described in DE-OS 197 36 906,
amide-ether carboxylic acids,
condensation products prepared from $C_8$-$C_{30}$ fatty alcohols with protein hydrolysates and/or amino acids and the derivatives thereof, which are known to a person skilled in the art as protein/fatty acid condensation products, such as for example Lamepon® grades, Gluadin® grades, Hostapon® KCG or Amisoft® grades.

Preferred anionic surfactants are alkyl sulfates, alkyl polyglycol ether sulfates and ether carboxylic acids having about 10 to about 18 C atoms in the alkyl group and up to about 12 glycol ether groups per molecule, sulfosuccinic acid mono- and dialkyl esters having about 8 to about 18 C atoms in the alkyl group and sulfosuccinic acid monoalkyl polyoxyethyl esters having about 8 to about 18 C atoms in the alkyl group and 1 to about 6 oxyethyl groups, monoglyceryl disulfates, alkyl and alkenyl ether phosphates and protein/fatty acid condensation products.

Cationic surfactants of the type including quaternary ammonium compounds, ester quats and amidoamines may furthermore be used. Preferred quaternary ammonium compounds are ammonium halides, in particular chlorides and bromides, such as alkyltrimethylammonium chlorides, dialkyldimethylammonium chlorides and trialkylmethylammonium chlorides. The long alkyl chains of these surfactants preferably comprise 10 to 18 carbon atoms, such as for example in cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Further preferred cationic surfactants are the imidazolium compounds known under the INCI names Quaternium-27 and Quaternium-83.

Those surface-active compounds which bear at least one quaternary ammonium group and at least one —COO$^{(-)}$ or —SO3$^{(-)}$ group on each molecule are designated as zwitterionic surfactants. Particularly suitable zwitterionic surfactants are "betaines" such as N-alkyl-N,N-dimethylammonium glycinates, for example cocoalkyldimethylammonium glycinate, N-acylaminopropyl-N,N-dimethylammonium glycinates, for example cocoacylaminopropyl-dimethylammonium glycinate, and 2-alkyl-3-carboxymethyl-3-hydroxyethylimidazolines having in each case about 8 to about 18 C atoms in the alkyl or acyl group and cocoacylaminoethylhydroxyethylcarboxymethyl glycinate. One preferred zwitterionic surfactant is the fatty acid amide derivative known by the INCI name Cocamidopropyl Betaine.

Ampholytes are taken to mean those surface-active compounds which, in addition to a $C_8$-$C_{24}$ alkyl or acyl group, contain at least one free amino group and at least one —COOH or —SO₃H group per molecule and are capable of forming internal salts. Examples of suitable ampholytes are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids with in each case about 8 to about 24 C atoms in the alkyl group. Particularly preferred ampholytes are N-cocoalkyl aminopropionate, cocoacylaminoethyl aminopropionate and $C_{12}$-$C_{18}$ acyl sarcosine.

The agents contain the ingredients or active substances in a cosmetically acceptable carrier.

Preferred cosmetically acceptable carriers are aqueous, alcoholic or aqueous/alcoholic media preferably comprising at least about 10 wt. % water, relative to the entire agent. Alcohols which may be present are in particular the lower alcohols with 1 to about 4 carbon atoms such as for example ethanol and isopropanol which are conventionally used for cosmetic purposes. It is preferred to use at least one ($C_1$ to $C_4$) monoalkyl alcohol in the agents in particular in a quantity of about 1 to about 50 wt. %, in particular of about 5 to about 30 wt. %. This is preferred in turn in particular for formulation as a pump mousse or aerosol mousse.

Additional cosolvents which may be present are organic solvents or a mixture of solvents with a boiling point of below about 400° C. in a quantity of about 0.1 to about 15 weight percent, preferably of about 1 to about 10 weight percent relative to the total agent. Particularly suitable additional cosolvents are unbranched or branched hydrocarbons such as pentane, hexane, isopentane and cyclic hydrocarbons such as cyclopentane and cyclohexane. Further, particularly preferred water-soluble solvents are glycerol, ethylene glycol and propylene glycol in a quantity of up to about 30 wt. % relative to the total agent.

In particular, adding glycerol and/or propylene glycol and/or polyethylene glycol and/or polypropylene glycol increases the flexibility of the polymer film formed on application of the agent. Accordingly, if a flexible hold is desired, the agents preferably contain about 0.01 to about 30 wt. % of glycerol and/or propylene glycol and/or polyethylene glycol and/or polypropylene glycol, relative to the entire agent.

The agents preferably have a pH value of about 2 to about 11. The pH range between about 2 and about 8 is more preferred. Details regarding pH value here relate for the purposes of the present document to the pH value at 25° C. unless otherwise stated.

The agents may further contain the auxiliary substances and additives which are usually added to conventional styling compositions.

Suitable auxiliary substances and additives which may be mentioned are in particular additional conditioning substances.

An example of a conditioning substance which may be used is a silicone oil and/or a silicone gum.

Suitable silicone oils or silicone gums are in particular dialkyl- and alkylarylsiloxanes, such as for example dimethylpolysiloxane and methylphenylpolysiloxane, and the alkoxylated, quaternized or also anionic derivatives thereof. Preference is given to cyclic and linear polydialkylsiloxanes, the alkoxylated and/or aminated derivatives thereof, dihydroxypolydimethylsiloxanes and polyphenylalkylsiloxanes.

Silicone oils bring about the most varied effects. For example, they simultaneously influence dry and wet combability, the feel of the dry and wet hair and its gloss. The term silicone oils is understood by a person skilled in the art to mean a plurality of organo-silicon compounds of different structures. The first among these are the dimethiconols. The following commercial products can be mentioned as examples of such products: Botanisil NU-150M (Botanigenics), Dow Corning 1-1254 fluid, Dow Corning 2-9023 fluid, Dow Corning 2-9026 fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzenesulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401DC (all above-stated from Chemsil Silicones, Inc.), Dow Corning 1401 fluid, Dow Corning 1403 fluid, Dow Corning 1501 fluid, Dow Corning 1784 HVF Emulsion, Dow Corning 9546 Silicone Elastomer Blend (all above-stated from Dow Corning Corporation), Dub Gel SI 1400 (Stearinerie Dubois Fils), HVM 4852 Emulsion (Crompton Corporation), Jeesilc 6056 (Jeen International Corporation), Lubrasil, Lubrasil DS (both from Guardian Laboratories), Nonychosine E, Nonychosine V (both from Exsymol), SanSurf Petrolatum-25, Satin Finish (both from Collaborative Laboratories, Inc.), Silatex-D30 (Cosmetic Ingredient Resources), Silsoft 148, Silsoft E-50, Silsoft E-623 (all above-stated from Crompton Corporation), SM555, SM2725, SM2765, SM2785 (all above-stated from GE Silicones), Taylor T-Sil CD-1, Taylor TME-4050E (all from Taylor Chemical Company), TH V 148 (Crompton Corporation), Tixogel CYD-1429 (Süd-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all above-stated from Wacker-Chemie GmbH).

Dimethicones form the second group of silicones which may be present. These may be both linear and branched and cyclic or cyclic and branched.

Dimethicone copolyols (S3) form a further group of silicones which are suitable. Corresponding dimethicone copolyols are commercially obtainable and are distributed, for example, by Dow Corning under the name Dow Corning® 5330 Fluid.

Of course, various embodiments also provide that the dimethiconols, dimethicones and/or dimethicone copolymers may already be present as an emulsion. In this case, the corresponding emulsion of dimethiconols, dimethicones and/or dimethicone copolyols may be produced both after the production of the corresponding dimethiconols, dimethicones and/or dimethicone copolyols from the latter and using the conventional methods of emulsification known to a person skilled in the art. To this end, any of cationic, anionic, nonionic or zwitterionic surfactants and emulsifiers may be used as auxiliary materials for producing the corresponding emulsions. The emulsions of the dimethiconols, dimethicones and/or dimethicone copolyols may, of course, also be produced directly by an emulsion polymerization method. Such methods are also well known to a person skilled in the art. If the dimethiconols, dimethicones and/or dimethicone copolyols are used as an emulsion, the droplet size of the emulsified particles amounts to about 0.01 to about 10000 microns (μm), preferably to about 0.01 to about 100 μm, more preferably to about 0.01 to about 20 μm and particularly preferably to about 0.01 to about 10 μm. Particle size is here determined using the light scattering method.

If branched dimethiconols, dimethicones and/or dimethicone copolyols are used, it should be understood that the branching is greater in this case than the chance branching which arises due to impurities in the respective monomers. For the purposes of this description, branched dimethiconols, dimethicones and/or dimethicone copolyols should accordingly be taken to mean that the degree of branching is greater than about 0.01%. Preferably, the degree of branching is greater than about 0.1% and particularly preferably greater than about 0.5%. The degree of branching is here determined from the ratio of the unbranched monomers to the branching monomers, i.e. the quantity of tri- and tetrafunctional siloxanes. Dimethiconols, dimethicones and/or dimethicone copolyols with both a low and a high degree of branching may be particularly preferred.

Particularly suitable silicones are amino-functional silicones, in particular those silicones covered by the INCI name Amodimethicone. It is therefore preferable for the agent to additionally contain at least one amino-functional silicone. These should be taken to include silicones which comprise at least one, optionally substituted, amino group. These silicones are denoted in accordance with the INCI Declaration as Amodimethicone and are obtained for example in the form of an emulsion as the commercial product Dow Corning® 939 or as the commercial product Dow Corning® 949 in a mixture with a cationic and a nonionic surfactant.

Preferably used amino-functional silicones are those which have an amine value of above about 0.25 meq/g, preferably of above about 0.3 meq/g and more preferably of above about 0.4 meq/g. The amine value here denotes the milliequivalents of amine per gram of the amino-functional silicone. It can be determined by titration and may also be stated in the unit mg of KOH/g.

The agents contain the silicones preferably in quantities of about 0.01 wt. % to about 15 wt. %, more preferably of about 0.05 to about 2 wt. %, relative to the total agent.

The agent may for example contain at least one protein hydrolysate and/or one of the derivatives thereof as a conditioning substance of another compound class.

Protein hydrolysates are product mixtures which are obtained by acidically, basically or enzymatically catalyzed degradation of proteins. The term "protein hydrolysates" is further defined to covers total hydrolysates and individual amino acids and the derivatives thereof and mixtures of different amino acids. The molecular weight of the protein hydrolysates which may be used is between about 75, the molecular weight of glycine, and about 200,000, the molecular weight preferably amounting to about 75 to about 50,000 and particularly preferably to about 75 to about 20,000 daltons.

Protein hydrolysates of both plant and animal origin or marine or synthetic origin may be used.

Animal protein hydrolysates are for example elastin, collagen, keratin, silk and milk protein hydrolysates which may also assume salt form. Such products are distributed for example under the tradenames Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

The protein hydrolysates are present in the agents for example in concentrations of about 0.01 wt. % up to about 20 wt. %, preferably of about 0.05 wt. % up to about 15 wt. % and particularly preferably in quantities of about 0.05 wt. % up to about 5 wt. %, in each case relative to the total preparation for use.

The agent may furthermore contain at least one vitamin, a provitamin, a vitamin precursor and/or one of the derivatives thereof as a conditioning substance.

Preferred vitamins, provitamins and vitamin precursors are those which are conventionally assigned to groups A, B, C, E, F and H.

The group of substances designated vitamin A includes retinol (vitamin $A_1$) and 3,4-didehydroretinol (vitamin $A_2$). β-Carotene is the provitamin of retinol. Examples of substances which may be considered as the vitamin A component are vitamin A acid and the esters thereof, vitamin A aldehyde and vitamin A alcohol and the esters thereof such as the palmitate and the acetate. The agents preferably contain the vitamin A component in quantities of from about 0.05-1 wt. %, relative to the total preparation for use.

The vitamin B group or the vitamin B complex include inter alia vitamin $B_1$ (thiamin), vitamin $B_2$ (riboflavin), vitamin $B_3$ (nicotinic acid and/or nicotinamide (niacinamide)), vitamin $B_5$ (pantothenic acid, panthenol and pantolactone), vitamin $B_6$ (pyridoxine and pyridoxamine and pyridoxal), vitamin C (ascorbic acid), vitamin E (tocopherols, in particular α-tocopherol), vitamin F (linoleic acid and/or linolenic acid), vitamin H.

The agents preferably contain vitamins, provitamins and vitamin precursors from the groups A, B, C, E and H. Panthenol, pantolactone, pyridoxine and the derivatives thereof and nicotinamide and biotin are more preferred.

D-panthenol, optionally in combination with at least one of the above-stated silicone derivatives, is particularly preferably used as a conditioning substance.

Like the addition of glycerol and/or propylene glycol, the addition of panthenol increases the flexibility of the polymer film formed using the agent. If a particularly flexible hold is desired, the agents may contain panthenol instead of or in addition to glycerol and/or propylene glycol. In a preferred embodiment, the agents contain panthenol, preferably in a quantity of about 0.05 to about 10 wt. %, more preferably about 0.1-5 wt. %, in each case relative to the total agent.

The agents may furthermore contain at least one plant extract as conditioning substance.

Conventionally, these extracts are produced by extraction of the entire plant. However, in individual cases it may also be preferable to produce the extracts solely from the blossoms and/or leaves of the plant.

Preference is above all given to extracts from green tea, oak bark, stinging nettle, witch hazel, hops, henna, chamomile, burdock root, horsetail, hawthorn, lime blossom, almond, aloe vera, pine-needle, horse chestnut, sandalwood, juniper, coconut, mango, apricot, lime, wheat, kiwi fruit, melon, orange, grapefruit, sage, rosemary, birch, mallow, lady's smock, wild thyme, yarrow, thyme, melissa, restharrow, coltsfoot, marsh mallow, meristem, ginseng and ginger root.

It may furthermore be preferred to use mixtures of a plurality of, in particular of two, different plant extracts in the agents.

Mono- or oligosaccharides may also be used as a conditioning substance in the agents. Both monosaccharides and oligosaccharides, such as for example cane sugar, lactose and raffinose, may be used. The use of monosaccharides is preferred. Among the monosaccharides, those compounds containing 5 or 6 carbon atoms are in turn preferred. Suitable pentoses and hexoses are for example ribose, arabinose, xylose, lyxose, allose, altrose, glucose, mannose, gulose, idose, galactose, talose, fucose and fructose. Arabinose, glucose, galactose and fructose are carbohydrates which are preferably used; glucose, which is suitable both in the D-(+) or L-(−) configuration or as racemate is particularly preferably used. Derivatives of these pentoses and hexoses, such as the corresponding -onic and -uronic acids (saccharic acids), sugar alcohols and glycosides, may furthermore be used.

Preferred saccharic acids are gluconic acid, glucuronic acid, saccharic acid, mannosaccharic acid and mucic acid. Preferred sugar alcohols are sorbitol, mannitol and dulcitol. Preferred glycosides are the methyl glucosides.

Since the mono- or oligosaccharides used are conventionally obtained from natural raw materials such as starch, they generally exhibit the configurations corresponding to these raw materials (for example D-glucose, D-fructose and D-galactose).

The mono- or oligosaccharides are preferably present in the agents in a quantity of about 0.1 to about 8 wt. %, more preferably 1 about to about 5 wt. %, relative to the total preparation for use.

The agent may furthermore contain at least one lipid as conditioning substance. Lipids which are suitable are phospholipids, for example soy lecithin, egg lecithin and cephalins and the substances known under the INCI names Linoleamidopropyl PG-Dimonium Chloride Phosphate, Cocamidopropyl PG-Dimonium Chloride Phosphate and Stearamidopropyl PG-Dimonium Chloride Phosphate. These are distributed for example by Mona under the trade names Phospholipid EFA®, Phospholipid PTC® and Phospholipid SVC®. The agents preferably contain the lipids in quantities of about 0.01 to about 10 wt. %, in particular of about 0.1 to about 5 wt. %, relative to the total preparation for use.

Oil bodies are furthermore suitable as a conditioning substance.

Natural and synthetic cosmetic oil bodies include, for example:
  vegetable oils. Examples of such oils are sunflower oil, olive oil, soy oil, rapeseed oil, almond oil, jojoba oil, orange oil, wheat germ oil, peach stone oil and the liquid fractions of coconut oil. However, other triglyceride oils such as the liquid fractions of beef fat together with synthetic triglyceride oils are also suitable.
  liquid paraffin oils, isoparaffin oils and synthetic hydrocarbons and di-n-alkyl ethers having a total of between about 12 and about 36 C atoms, in particular about 12 to about 24 C atoms, such as for example di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether and n-hexyl-n-undecyl ether and di-tert-butyl ether, di-iso-pentyl ether, di-3-ethyldecyl ether, tert-butyl-n-octyl ether, iso-pentyl-n-octyl ether and 2-methylpentyl-n-octyl ether. The compounds 1,3-di-(2-ethylhexyl)cyclohexane (Cetiol® S) and di-n-octyl ether (Cetiol®OE) available as commercial products may be preferred.
  ester oils. Ester oils should be taken to mean the esters of $C_6$-$C_{30}$ fatty acids with $C_2$-$C_{30}$ fatty alcohols. The monoesters of fatty acids with alcohols having about 2 to about 24 C atoms are preferred. More preferred substances are isopropyl myristate (Rilanit® IPM), isononanoic acid $C_{16-18}$ alkyl ester (Cetiol® SN), 2-ethylhexyl palmitate (Cegesoft® 24), stearic acid 2-ethylhexyl ester (Cetiol® 868), cetyl oleate, glycerol tricaprylate, coco fatty alcohol caprate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® mm), cetearyl isononanoate (Cetiol® SN), oleic acid decyl ester (Cetiol® V).
  dicarboxylic acid esters such as di-n-butyl adipate, di-(2-ethylhexyl) adipate, di-(2-ethylhexyl) succinate and diisotridecyl acelate and diol esters such as ethylene glycol dioleate, ethylene glycol diisotridecanoate, propylene glycol di(2-ethylhexanoate), propylene glycol diisostearate, propylene glycol dipelargonate, butanediol diisostearate, neopentyl glycol dicaprylate,
  symmetrical, asymmetrical or cyclic esters of carbonic acid with fatty alcohols, for example described in DE-OS 197 56 454, glycerol carbonate or dicaprylyl carbonate (Cetiol® CC),
  trifatty acid esters of saturated and/or unsaturated linear and/or branched fatty acids with glycerol,
  fatty acid partial glycerides, which are taken to mean monoglycerides, diglycerides and the technical mixtures thereof. When using technical products, small quantities of triglycerides may still be contained therein, depending on the production method. Partial glycerides are preferably of formula (D4-I),

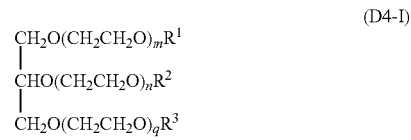

(D4-I)

in which $R^1$, $R^2$ and $R^3$ mutually independently denote hydrogen or a linear or branched, saturated and/or unsaturated acyl residue with about 6 to about 22, preferably about 12 to about 18, carbon atoms, with the proviso that at least one of these groups denotes an acyl residue and at least one of these groups denotes hydrogen. The sum (m+n+q) denotes 0 or numbers from 1 to 100, preferably 0 or 5 to about 25. Preferably, $R^1$ denotes an acyl residue and $R^2$ and $R^3$ denote hydrogen and the sum (m+n+q) is 0. Typical examples are mono- and/or diglycerides based on caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and the technical mixtures thereof. Preferably, oleic acid monoglycerides are used.

The input quantity of the natural and synthetic cosmetic oil bodies in the agents conventionally amounts to about 0.1-30 wt. %, relative to the total preparation for use, preferably about 0.1-20 wt. %, and in particular about 0.1-15 wt. %.

Although each of the stated conditioning substances itself alone gives rise to a satisfactory result, in exemplary embodiments the agent contains a plurality of conditioning substances, including from different groups.

Through the addition of a UV filter, both the agents themselves and the treated fibers may be protected from the harmful effects of UV radiation. At least one UV filter is accordingly preferably added to the agent. Suitable UV filters are not subject to any general restrictions with regard to structure and physical properties. Rather, any UV filters usable in the field of cosmetics whose absorption maximum is in the UVA (315-400 nm), the UVB (280-315 nm) or the UVC (<280 nm) range are suitable. UV filters with an absorption maximum in the UVB range, in particular in the range from approx. 280 to approx. 300 nm, are more preferred.

The UV filters preferred may for example be selected from substituted benzophenones, p-aminobenzoic acid esters, diphenylacrylic acid esters, cinnamic acid esters, salicylic acid esters, benzimidazoles and o-aminobenzoic acid esters.

Examples of UV filters usable are 4-aminobenzoic acid, N,N,N-trimethyl-4-(2-oxoborn-3-ylidenemethyl)aniline methylsulfate, 3,3,5-trimethylcyclohexyl salicylate (homosalate), 2-hydroxy-4-methoxybenzophenone, 2-phenylbenzimidazole-5-sulfonic acid and the potassium, sodium and triethanolamine salts thereof, 3,3'-(1,4-phenylenedimethylene)-bis(7,7-dimethyl-2-oxobicyclo-[2.2.1]hept-1-yl-methanesulfonic acid) and the salts thereof, 1-(4-tert-butylphenyl)-3-(4-methoxyphenyl)propane-1,3-dione, α-(2-oxoborn-3-ylidene)-toluene-4-sulfonic acid and the salts thereof, ethoxylated 4-aminobenzoic acid ethyl ester (PEG-25 PABA; Uvinul®P 25), 4-dimethylaminobenzoic acid 2-ethylhexyl ester, salicylic acid 2-ethylhexyl ester, 4-methoxycinnamic acid isopentyl ester, 4-methoxycinnamic acid 2-ethylhexyl ester, 2-hydroxy-4-methoxybenzophenone-5-sulfonic acid and the sodium salt thereof (benzophenone-4; Uvinul®MS 40; Uvasorb®S 5), 3-(4'-methylbenzylidene)-D,L-camphor, 3-benzylidenecamphor (3-benzylidene camphor), 4-isopropylbenzyl salicylate 2,4,6-trianilino-(p-carbo-2'-ethylhexyl-1'-oxy)-1,3,5-triazine, 3-imidazol-4-ylacrylic acid and the ethyl esters thereof, polymers of N-{(2 and 4)-[2-oxoborn-3-ylidenemethyl]benzyl}-acrylamide, 2,4-dihydroxybenzophenone, 1,1'-diphenylacrylonitrile acid 2-ethylhexyl ester, o-aminobenzoic acid menthyl ester, 2,2',4,4'-tetrahydroxybenzophenone, 2,2'-dihydroxy-4,4'-dimethoxybenzophenone, 2,2'-dihydroxy-4,4'-dimethoxybenzophenone-5-sodium sulfonate and 2-cyano-3,3-diphenylacryl acid 2'-ethylhexyl ester. 2-hydroxy-4-methoxybenzophenone 5-sulfonic acid and the sodium salt thereof and/or ethoxylated 4-aminobenzoic acid ethyl ester are preferred.

The UV filters are conventionally present in quantities of about 0.01-5 wt. %, relative to the total preparation for use. Quantities of about 0.1-2.5 wt. % are preferred.

In one particular embodiment, the agent furthermore contains one or more substantive dyes. This makes it possible, when applying the composition, for the treated keratinic fibers not only to be temporarily structured but also to be dyed at the same time. This may be particularly desirable when only temporary coloring, for example with conspicuous fashion colors, is desired, which may be removed again from the keratinic fibers simply by washing.

Substantive dyes are conventionally nitrophenylenediamines, nitroaminophenols, azo dyes, anthraquinones or indophenols. Preferred substantive dyes are the compounds known by the international names or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52 as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-1-hydroxy-4-nitrobenzene. Cationic substantive dyes are preferably used. Greater preference is here given to (a) cationic triphenylmethane dyes, such as for example Basic Blue 7, Basic Blue 26, Basic Violet 2 and Basic Violet 14,
(b) aromatic systems substituted with a quaternary nitrogen group, such as for example Basic Yellow 57, Basic Red 76, Basic Blue 99, Basic Brown 16 and Basic Brown 17, as well as
(c) substantive dyes containing at least one heterocycle which comprises at least one quaternary nitrogen atom, as are for example mentioned in claims 6 to 11 of EP-A2-998 908, to which explicit reference is here made.

The dyes which are also known by the names Basic Yellow 87, Basic Orange 31 and Basic Red 51 are particularly preferred cationic substantive dyes of the group (c). The cationic substantive dyes distributed under the trademark Arianor® are cationic substantive dyes which are likewise particularly preferred.

The agents according to this embodiment preferably contain the substantive dyes in a quantity of about 0.001 to about 20 wt. %, relative to the total agent.

It is preferred for the agents to be free of oxidation dye precursors. Oxidation dye precursors are divided into "developer components" and "coupler components". Under the influence of oxidizing agents or of atmospheric oxygen, the developer components develop the actual dyes through action with one another or through coupling with one or more coupler components.

The agents may be formulated in any forms conventional for styling agents, for example in the form of solutions, which may be applied onto the hair as a hair lotion or pump or aerosol spray, in the form of creams, emulsions, waxes, gels or also surfactant-containing foaming solutions or other preparations which are suitable for application onto the hair.

Hair creams and hair gels generally contain structuring agents and/or thickening polymers which serve to impart the desired consistency to the products. Structuring agents and/or thickening polymers are typically used in a quantity of about 0.1 to about 10 wt. %, relative to the entire product. Quantities of about 0.5 to about 5 wt. %, in particular of about 0.5 to about 3 wt. %, are preferred.

The agents are preferably formulated as pump sprays, aerosol sprays, pump mousses or aerosol mousses.

To this end, the agents are packaged in a release device which is either a pressurized gas container ("aerosol container") additionally filled with a propellant or a non-aerosol container.

Pressurized gas containers, in which a product is distributed through the internal gas pressure of the container via a valve, are known by definition as "aerosol containers". Conversely, the term "non-aerosol container" defines a container at normal pressure, in which a product is distributed by means of mechanical action through a pump system.

The agents are more preferably formulated as aerosol hair mousse or aerosol hair spray. The agent (in particular the preferred embodiments (A) to (F) (see above)) therefore preferably additionally contains at least one propellant.

Propellants which are for example selected from $N_2O$, dimethyl ether, $CO_2$, air, alkanes with about 3 to about 5 carbon atoms, such as propane, n-butane, iso-butane, n-pentane, and iso-pentane, and mixtures thereof. Dimethyl ether, propane, n-butane, iso-butane and mixtures thereof are preferred.

According to a preferred embodiment, the stated alkanes, mixtures of the stated alkanes or mixtures of the stated alkanes with dimethyl ether are used as the sole propellant. In other embodiments, however, co-use of propellants of the chlorofluorocarbon type, but especially of the fluorocarbon type, are explicitly encompassed.

With a given spray device, the size of the aerosol particles or of the mousse bubbles and the respective size distribution may be established by the quantity ratio of propellant to the other components of the preparations.

The quantity of propellant used varies as a function of the specific composition of the agent, of the packaging used and of the desired product type, for instance hair spray or hair mousse. When using conventional spray devices, aerosol mousse products preferably contain the propellant in quantities of about 1 to about 35 wt. %, relative to the entire product. Quantities of about 2 to about 30 wt. %, in particular of about 3 to about 15 wt. %, are more preferred. Aerosol sprays generally contain larger quantities of propellant. In this case, the propellant is preferably used in a quantity of about 30 to about 98 wt. %, relative to the entire product. Quantities of about 40 to about 95 wt. %, in particular of about 50 to about 95 wt. %, are more preferred.

Aerosol products may be manufactured in conventional manner. In general, all the components of the particular agent, with the exception of the propellant, are introduced into a suitable pressure-resistant container. The latter is then closed with a valve. The desired quantity of propellant is then finally introduced using conventional methods.

To foam gel-form agents in a two-chamber aerosol container, isopentane is preferably suitable as a propellant which is incorporated into the agents and is packaged in the first chamber of the two-chamber aerosol container. At least one further propellant different from isopentane is packaged in the second chamber of the two-chamber aerosol container, said further propellant developing a higher pressure than the isopentane in the two-chamber aerosol container. The propellants in the second chamber are preferably selected from $N_2O$, dimethyl ether, $CO_2$, air, alkanes with 3 or 4 carbon atoms (such as propane, n-butane, iso-butane) and mixtures thereof.

A preferred embodiment of the agents are aerosol hair mousses or aerosol hair sprays, containing the above-described agent and at least one propellant.

Preferred agents and propellants of the aerosol hair mousse or aerosol hair spray and the respective quantities of propellant are in line with the above explanations.

Exemplary embodiments secondly provide use of the agents for temporarily deforming hair and/or for hair care.

The agents and products containing these agents, in particular aerosol hair mousses or aerosol hair sprays, are distinguished in particular in that they impart a very strong, durable styling hold to treated hair while leaving the hair flexible. If the agent is formulated as hair mousse, a stable, fine-pored, creamy mousse is formed, which can be distributed on the hair evenly and without dripping.

An exemplary embodiment thirdly provides a method for treating keratin-containing fibers, in particular human hair, in which an agent according to the first subject matter is foamed using a release device to yield a mousse and the resultant mousse is applied to the keratin-containing fibers.

It is preferred for the keratin-containing fibers to be shaped and for this shape to be fixed by the agent constituting the first subject matter.

The above-stated release devices (see above) are preferred.

Exemplary embodiments fourthly provide a method for treating keratin-containing fibers, in particular human hair, in which an agent according to the first subject matter is applied as a spray to the keratin-containing fibers using a release device.

It is preferred for the keratin-containing fibers to be shaped and for this shape to be fixed by the agent constituting the first subject matter.

The above-stated release devices (see above) are preferred.

EXAMPLES

The quantities given below are in weight percent unless stated otherwise.

The following formulations were provided by mixing the stated raw materials:

| Raw materials | Invention 1 | Comparison 1 | Comparison 2 |
|---|---|---|---|
| 2-Amino-2-methylpropan-1-ol | 0.067 | — | 0.134 |
| Copolymer 937[1] | 3.75 | 7.50 | — |
| Gantrez ES 425[2] | 1.50 | | 3.00 |
| Water | | ad 100 | |

[1]INCI name: VP/Dimethylaminoethyl Methacrylate Copolymer (20 wt. % active substance in ethanol/water mixture, average molecular weight (Mw) 1000000) (Ashland),
[2]Copolymer of methyl vinyl ether and the butyl semi-ester of maleic acid (50 wt. % active substance in ethanol) INCI name: Butyl Ester of PVM/MA Copolymer (Ashland)

Standardized strands of hair from Kerling (item no. 827560) of the "European Natural" hair type, color 6/0 of a length ($L_{max}$) of 220 mm and a weight of 0.6 g were used. The strands were washed with a 12.5 wt. % sodium laureth sulfate solution by way of preparation. The strands of hair were dried overnight in a drying oven at 318 K.

0.18 g of the compositions were applied onto a strand of hair and rubbed in. The strand was then wound onto a curler (Fripac-medis, diameter 7 mm, item no. D-1203) and dried overnight at room temperature.

The curlers were carefully removed and the strands hung up. The length of the curls were in each case measured ($L_0$) and the strands placed in a conditioning cabinet. They were stored there at 294 K and a relative atmospheric humidity of 85% over a period of 24 h, after which the length of the curls was remeasured ($L_t$).

Five test strands per composition were correspondingly treated and measured.

High Humidity Curl Retention (HHCR) was calculated according to the following formula and the arithmetic mean of the HHCR values for the 5 test strands was determined for each composition:

$$HHCR = \frac{L_{max} - L_t}{L_{max} - L_0}$$

HHCRInvention 1: 83%
HHCRComparison 1: 32%
HHCRComparison 2: 29%

The polymer combination of the agent Invention 1 (a total of 1.5 wt. % polymer active substance) has a significantly higher HHCR than the same amount of polymer (1.5 wt. % active substance) of the in each case individual polymer of the comparison compositions Comparison 1 and Comparison 2.

While at least one exemplary embodiment has been presented in the foregoing detailed description, it should be appreciated that a vast number of variations exist. It should also be appreciated that the exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

The invention claimed is:

1. An agent for cosmetic treatment of keratin-containing fibers, in particular human hair, comprising:
   (a) about 0.1 wt. % to about 5.0 wt. %, relative to the weight of the agent, of at least one copolymer (a) comprising at least one structural unit of formula (I) and at least one structural unit of formula (II),

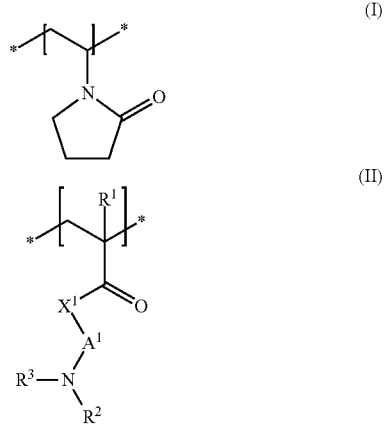

in which
R$^1$ denotes a hydrogen atom or a methyl group,
X$^1$ denotes an oxygen atom or an NH group,
A1 denotes an ethane-1,2-diyl, propane-1,3-diyl or butane-1,4-diyl group,
R$^2$ and R$^3$ mutually independently denote a (C$_1$ to C$_4$) alkyl group,
and
   (b) about 0.1 wt. % to about 5.0 wt. %, relative to the weight of the agent, of at least one copolymer (b) comprising at least one structural unit of formula (A1) and at least one structural unit of formula (A2)

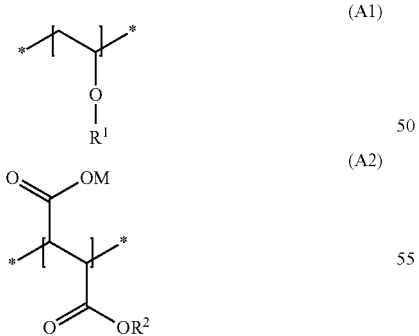

in which
R$^1$ denotes a (C$_1$ to C$_8$) alkyl group,
R$^2$ denotes a (C$_1$ to C$_6$) alkyl group,
M denotes a hydrogen atom or an equivalent of a mono- or polyvalent cation; and
a cosmetically acceptable carrier
wherein the ratio (W/W) of the at least one copolymer (a) to the at least one copolymer (b) is about 5:1 to 1:5.

2. The agent according to claim 1 wherein R$^1$ of formula (II) consists of a methyl group.

3. The agent according to claim 1 wherein A$^1$ of formula (II) consists of ethane-1,2-diyl or propane-1,3-diyl.

4. The agent according to claim 1 wherein R$^2$ and R$^3$ of formula (II) independently consists of methyl, ethyl, or a combination thereof.

5. The agent according to claim 1 wherein the copolymer (a) consists of a copolymer of N-vinylpyrrolidone and N,N-dimethylaminoethyl methacrylate.

6. The agent according to claim 1 wherein the copolymer (a) has an average molecular weight M$_w$ (weight-average) of about 50,000 grams per mole (g/mol) to about 50,000,000 g/mol.

7. The agent according to claim 1 wherein R1 of formula (A1) consists of a methyl group.

8. The agent according to claim 1 wherein R2 of formula (A2) consists of a (C$_2$ to C$_4$) alkyl group.

9. The agent according to claim 1 further comprising at least one alkanolamine.

10. A method of temporarily deforming hair and/or for hair care, the method comprising the steps of:
    applying an agent to the hair, wherein the agent comprises;
    (a) about 0.1 wt. % to about 5.0 wt. %, relative to the weight of the agent, of at least one copolymer (a) comprising at least one structural unit of formula (I) and at least one structural unit of formula (II),

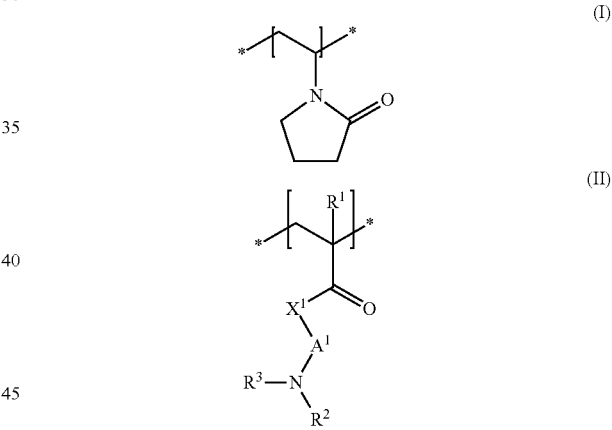

in which
R$^1$ denotes a hydrogen atom or a methyl group,
X$^1$ denotes an oxygen atom or an NH group,
A1 denotes an ethane-1,2-diyl, propane-1,3-diyl or butane-1,4-diyl group,
R$^2$ and R$^3$ mutually independently denote a (C$_1$ to C$_4$) alkyl group; and
   (b) about 0.1 wt. % to about 5.0 wt. %, relative to the weight of the agent, of at least one copolymer (b) comprising at least one structural unit of formula (A1) and at least one structural unit of formula (A2)

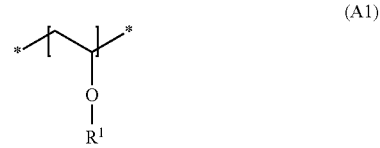

-continued

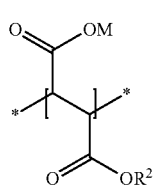

(A2)

in which
R¹ denotes a ($C_1$ to $C_8$) alkyl group,
R² denotes a ($C_1$ to $C_6$) alkyl group,
M denotes a hydrogen atom or an equivalent of a mono- or polyvalent Cation
wherein the ratio (W/W) of the at least one copolymer (a) to the at least one copolymer (b) is about 5:1 to 1:5.

11. The method of claim 10 further comprising:
foaming the agent from a release device to form a mousse; and
applying the mousse onto the hair.

12. The method of claim 10 further comprising:
spraying the agent from a release device onto the hair.

13. The agent according to claim 1 wherein the copolymer (a) has an average molecular weight $M_w$ (weight-average) of about 750,000 grams per mole (g/mol) to about 2,000,000 g/mol.

14. The agent according to claim 1 wherein R² of formula (A2) consists of an ethyl, n-propyl, isopropyl, n-butyl or tertiary butyl group.

15. The agent according to claim 1 wherein copolymer (b) is present in a quantity of about 0.2 wt. % to about 2.5 wt. % relative to the weight of the agent.

16. The agent according to claim 1 wherein the copolymer (a) is present in a quantity of about 0.2 weight percent (wt. %) to about 2.5 wt. % relative to the weight of the agent.

17. The agent according to claim 1, wherein the ratio (W/W) of the at least one copolymer (a) to the at least one copolymer (b) is about 2:1 to 1:2.

* * * * *